United States Patent
Nealon

(10) Patent No.: US 7,275,550 B2
(45) Date of Patent: Oct. 2, 2007

(54) APPARATUS AND METHOD FOR CLEANING AND PRESSURE TESTING TUBULAR STRUCTURES

(75) Inventor: Joseph M. Nealon, Woodland Hills, CA (US)

(73) Assignee: The Boeing Company, Chicago, IL (US)

( * ) Notice: Subject to any disclaimer, the term of this patent is extended or adjusted under 35 U.S.C. 154(b) by 428 days.

(21) Appl. No.: 10/838,048

(22) Filed: May 3, 2004

(65) Prior Publication Data

US 2005/0241677 A1 Nov. 3, 2005

(51) Int. Cl.
*B08B 9/02* (2006.01)
*B08B 3/04* (2006.01)

(52) U.S. Cl. ............... 134/22.1; 134/22.12; 134/26; 134/27

(58) Field of Classification Search ............ 134/22.11, 134/22.12, 24, 26, 22.1
See application file for complete search history.

(56) References Cited

U.S. PATENT DOCUMENTS

| | | | |
|---|---|---|---|
| 1,892,093 A * | 12/1932 | Battistella et al. ............ 134/10 |
| 4,458,522 A | 7/1984 | Toelke |
| 4,599,890 A | 7/1986 | Girone et al. |
| 4,646,561 A | 3/1987 | Toelke |
| 4,859,276 A | 8/1989 | John, Jr. et al. |
| 4,863,555 A | 9/1989 | John, Jr. et al. |
| 4,893,494 A | 1/1990 | Hart |
| 5,232,299 A | 8/1993 | Hiss |
| 5,295,392 A | 3/1994 | Hensel et al. |
| 5,549,759 A * | 8/1996 | Lithander ............... 134/22.11 |
| 5,678,584 A | 10/1997 | O'Brien |
| 5,680,877 A * | 10/1997 | Edstrand et al. .......... 134/103.1 |
| 6,450,182 B2 * | 9/2002 | Fillipi et al. ............... 134/22.1 |
| 6,645,310 B2 | 11/2003 | Rinne |

* cited by examiner

*Primary Examiner*—Michael Barr
*Assistant Examiner*—Saeed Chaudhry
(74) *Attorney, Agent, or Firm*—Alston & Bird LLP

(57) ABSTRACT

An apparatus and method for cleaning and pressure testing tube structures comprising a cleaning fluid supply pump and a pressurization pump alternately in fluid communication with a feed header having a feed header interface engageable to an end of at least one tube structure and a drain header having a drain header interface engageable to an opposing end of the at least one tube structure and an outlet valved so as to be selectively closed or opened depending on mode of operation of the apparatus. The apparatus and associated method cleans and pressure tests a tube by engaging a tube between the feed header interface and the drain header interface and maintaining said engagement while sequentially flowing a cleaning fluid through the inner diameter of the hollow tube, pressurizing a static fluid within the hollow tube, and releasing fluid from the tube.

19 Claims, 4 Drawing Sheets

APPARATUS AND METHOD FOR CLEANING AND PRESSURE TESTING TUBULAR STRUCTURES

FIELD OF THE INVENTION

The present invention relates to the manufacture of metal tubes, pump housings, manifolds, and welded assemblies, and, more particularly, to the cleaning and pressure testing of tubes, pump housings, manifolds, and welded assemblies, after fabrication.

BACKGROUND OF THE INVENTION

Tubular metallic structures, pump housings, manifolds, and welded assemblies (collectively referred to as "tubular structures") are commonly manufactured for use in a variety of applications, such as industrial machinery, automobiles, and aerospace applications. Newly fabricated tubular structures undergo a number of cleaning and testing phases before they are passed on for actual use. For instance, when a tube is used as a transport medium for liquids or gases, the inside of the tube must be cleaned to ensure that the inside of the tube is free of contaminants and debris that might contaminate the fluid being transported. When a tubular structure is to be used for transport of high-pressure fluids, the structure must be properly pressure tested to verify structural integrity prior to use.

The cleaning of the interior of tubes and similar components with relatively small diameter interior passages and those which include throughout their length a number of bent or curved portions, is especially difficult, primarily as the result of the difficulty of inserting conventional tools or other cleaning apparatus into the part and moving it along the full tube or interior passage length. A common technique for cleaning metal parts including the interior of tubes has been the use of so-called degreasing or vapor degreasing agents in which the parts are immersed in or exposed to a quantity of the cleaning liquid or vapor. This approach has been adopted extensively in the metal finishing industry.

Depending upon the ultimate use for the parts, the required cleanliness of the internal surfaces can vary considerably. In the case of gaseous oxygen or hydraulic lines used in aircraft or lines that carry liquid oxygen in missiles, for example, the tubes must be kept extremely clean and this requirement, of course, requires a more intensive cleaning operation. In the past, even when known highly efficient vapor degreasing agents were used, many hydraulic line tubing configurations had to be individually flushed with a solvent liquid in order to achieve the required high degree of cleanliness. As might be predicted, this resulted in a labor intensive and relatively expensive cleaning operation.

In addition to cleaning, proof pressure testing is used to verify the mechanical integrity of a fabricated structure. In typical pressure testing, the structure is filled with a type of fluid, either liquid (typically water) or gas (typically nitrogen), and pressurized to one and a half times the maximum operating pressure that the part is designed to operate with. The pressure is held for a period of time and then the pressure is released. The pressure cycle may be repeated multiple times as required to prove the structural integrity of the structure.

A typical pressure test system consists of a blast cell rated to contain the burst energy of the part being tested, a pump or accumulator to supply the required pressure, regulators and pressure gauges to regulate and measure the supplied pressure, relief valves to protect the system in the event of over pressurization, and various valves to direct and vent off pressure.

The processes of cleaning the various parts and pressure testing the various parts are both laborious and time consuming. In fact, in the mass production of tubular structures, cleaning and pressure testing are often the bottleneck in production schedules due to the need to set up special equipment for each task and the need to wait for equipment availability before each new part or set of parts may be cleaned or tested.

It is desired to provide a system and apparatus that would alleviate some of the problems associated with cleaning and pressure testing tubular structures. Particularly, it is desired to provide a system and apparatus that would reduce production time required to complete cleaning and pressure testing. Further, it is desired to provide a system and apparatus that would simplify the process steps required to clean and pressure test the tubular structures.

SUMMARY OF THE INVENTION

The invention is an apparatus and method capable of cleaning the inside of hollow tube structures, welded assemblies, pump housings, and manifolds (collectively "tubular structures" or simply "parts") and pressure testing the hollow tubular structures without the need to reconfigure, reposition, or relocate the tubular structures between the cleaning and testing phases. As such, the cleaning and testing phases may be streamlined so as to reduce overall production time.

The invented apparatus generally comprises a feed portion and an outlet portion. The feed portion of the apparatus is connectable to an inlet end of at least one tubular structure and provides fluid into the at least one tubular structure during operation of the apparatus. The feed portion of the apparatus comprises a feed valve network having an inlet and outlet wherein the inlet is selectively operable to provide communication with either a cleaning fluid supply pump, a rinse water pump, or a pressurization pump, and the outlet of the feed valve network is in fluid communication with a feed header having a feed header interface engageable with the at least one inlet end of the tubular structure.

The outlet portion of the apparatus is connectable to an outlet end of the at least one tubular structure and permits fluid to exit the at least one tubular structure during at least one phase of operation of the apparatus. The outlet portion of the apparatus comprises a drain header having a drain header interface that is engageable with an outlet end of the at least one tubular structure and is in fluid communication with an outlet valve network that is selectively closed or open.

The interfaces of the feed and drain headers are engageable to opposing ends of the at least one tube structure such that the inside of the at least one tubular structure is in fluid communication with both headers during operation of the apparatus. The interface seals the tube up to high-pressures for use in pressure testing. A typical pressure test would test the tube at up to 22,000 psi, so the interface would provide a seal up to that pressure during use. An exemplary interface is part interface no. F-250-C, available from Autoclave Engineers, Inc., Erie, Pa.

In operation, one or multiple production parts are cleaned and pressure tested by engaging an inlet of the at least one tubular structure to the interface of the feed header, engaging an outlet end of the at least one tubular structures to an input interface of the drain manifold, and maintaining engagement of the first and second ends of the at least one tubular structure with the respective manifolds while sequentially flowing a cleaning fluid through the inner diameter of the part, pressurizing a static fluid within the part, and releasing fluid from the part.

The flow of cleaning fluid through the tubular structures cleans any oil, solvents, or debris from the inside of the parts. Pressurizing a fluid within the parts to above the rated service pressure of the parts provides assurance that the parts are mechanically sound and suitable for its intended purpose. The ability to both clean and pressure test the tube while the tube is affixed to a single apparatus allows both operations to be accomplished with less setup time, wait time, and capital expense relative to conventional techniques that utilize multiple machines to accomplish those functions.

BRIEF DESCRIPTION OF THE DRAWINGS

Figure 1:
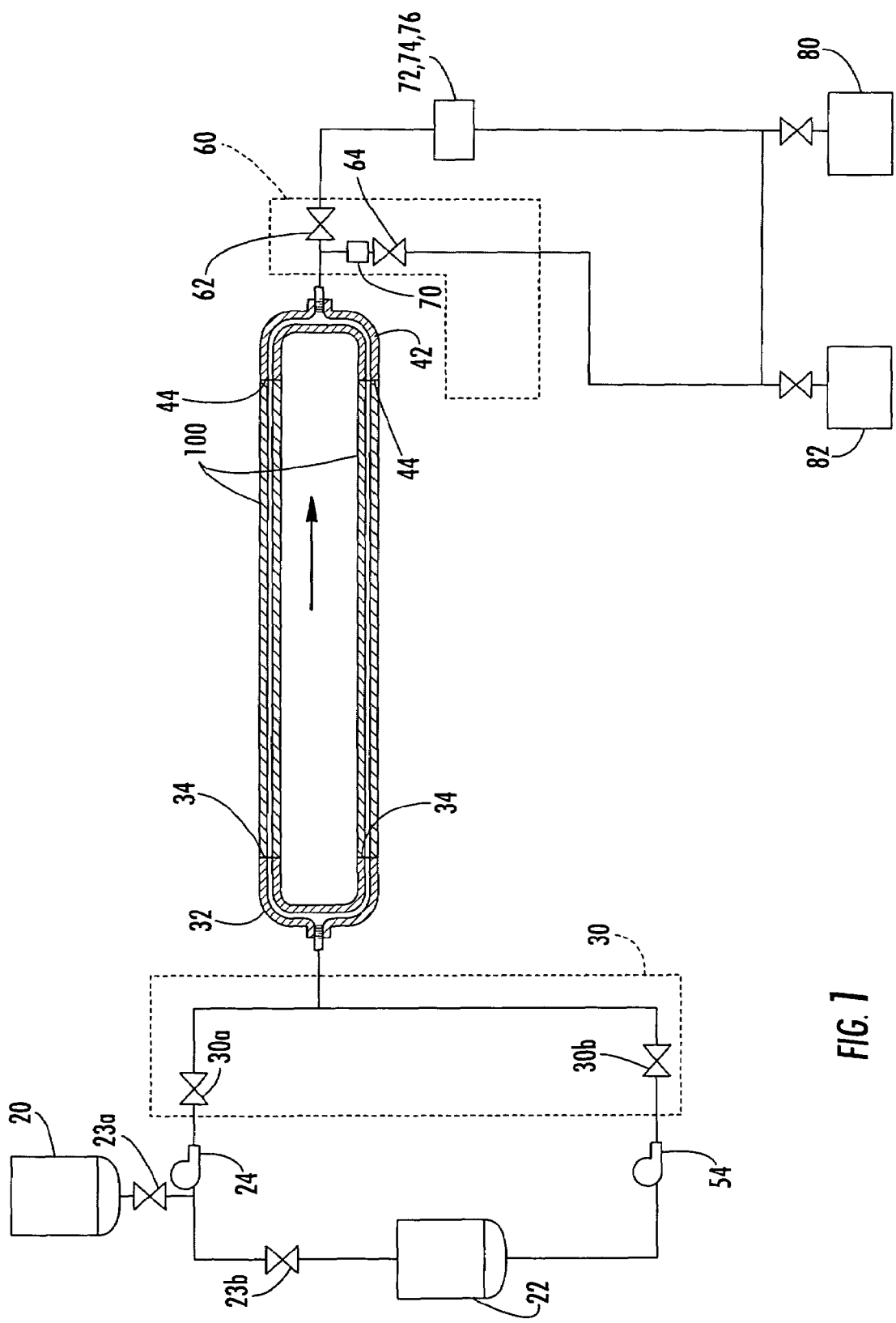
Figure 2:
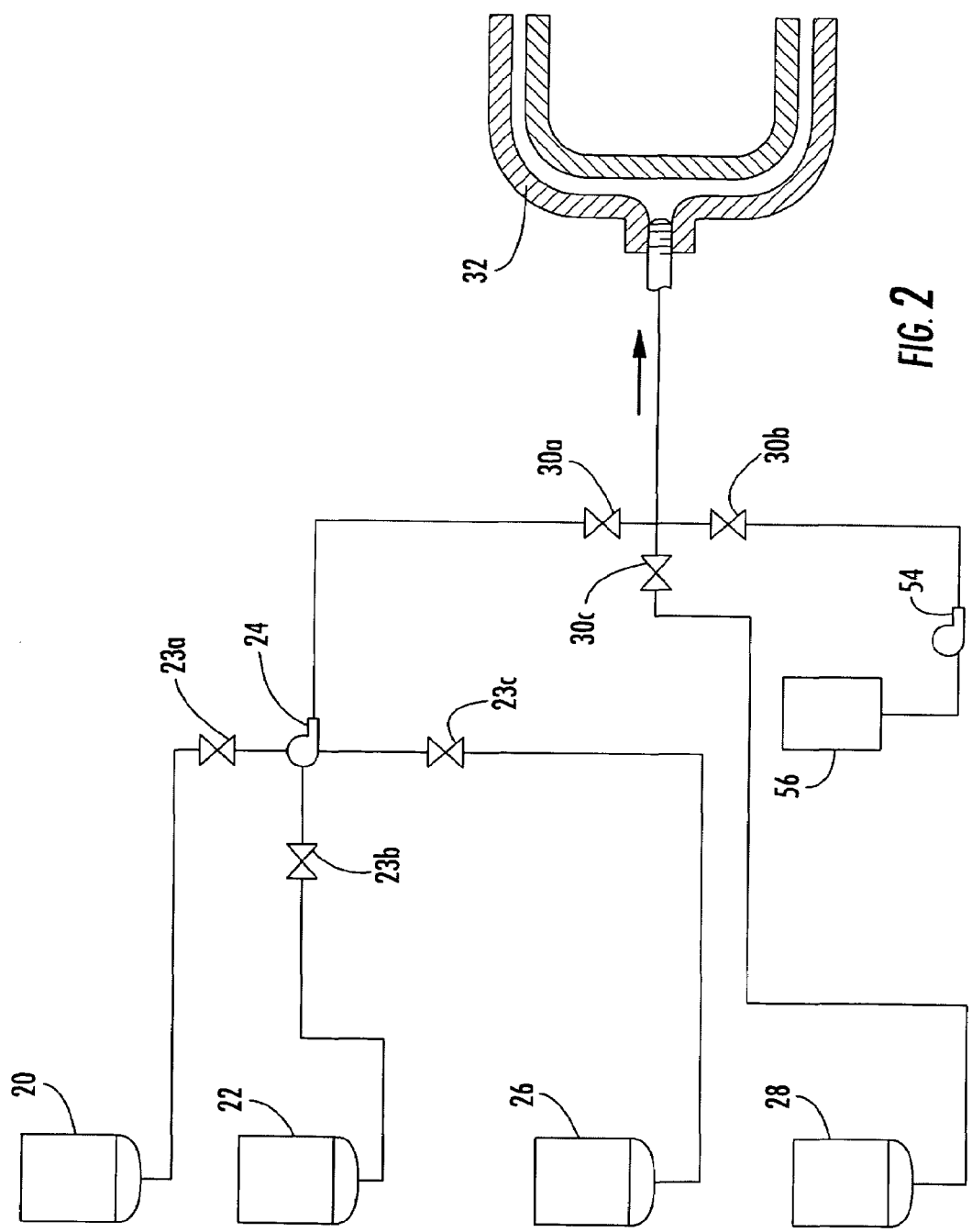
Figure 3:
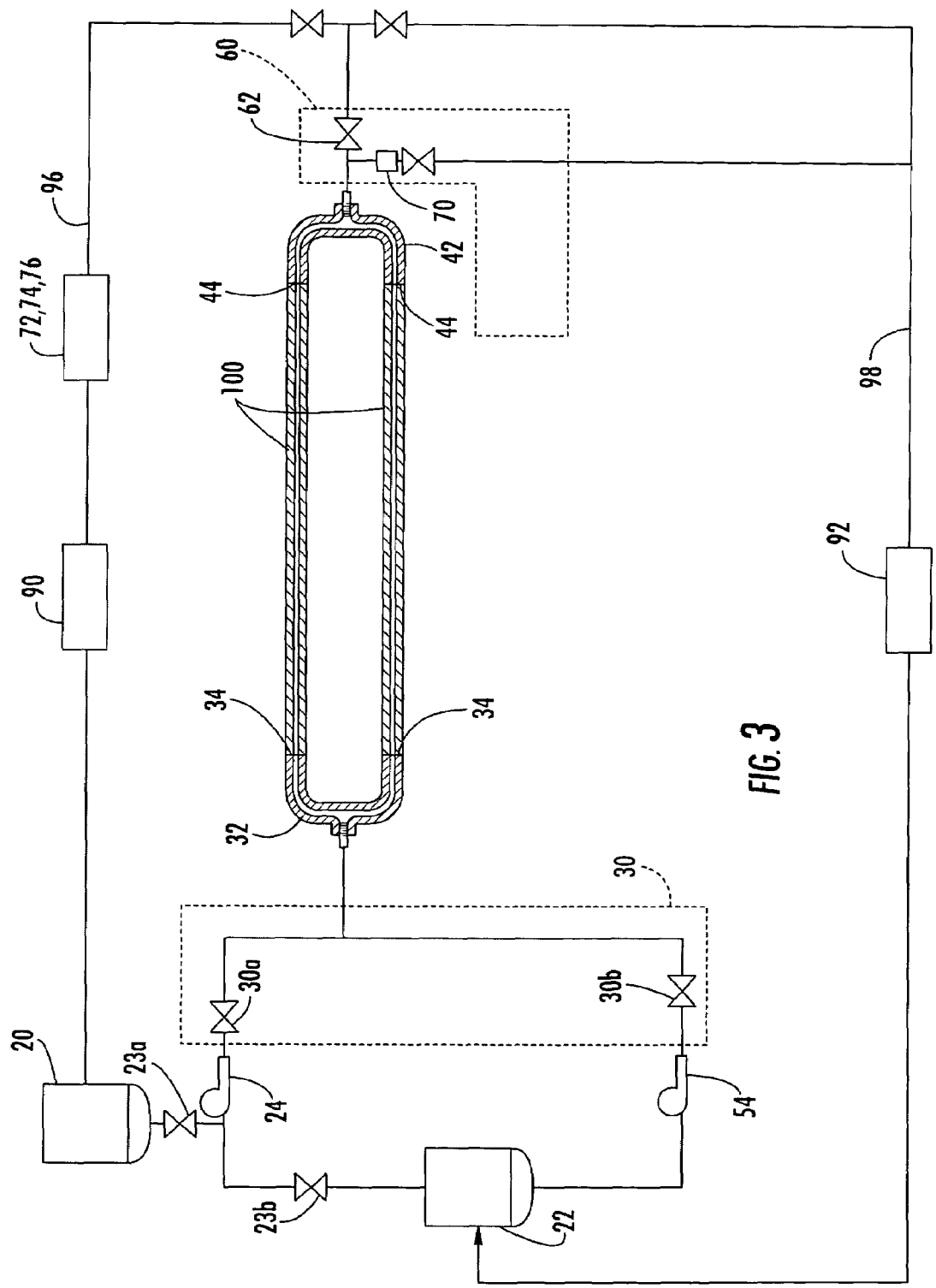
Figure 4:
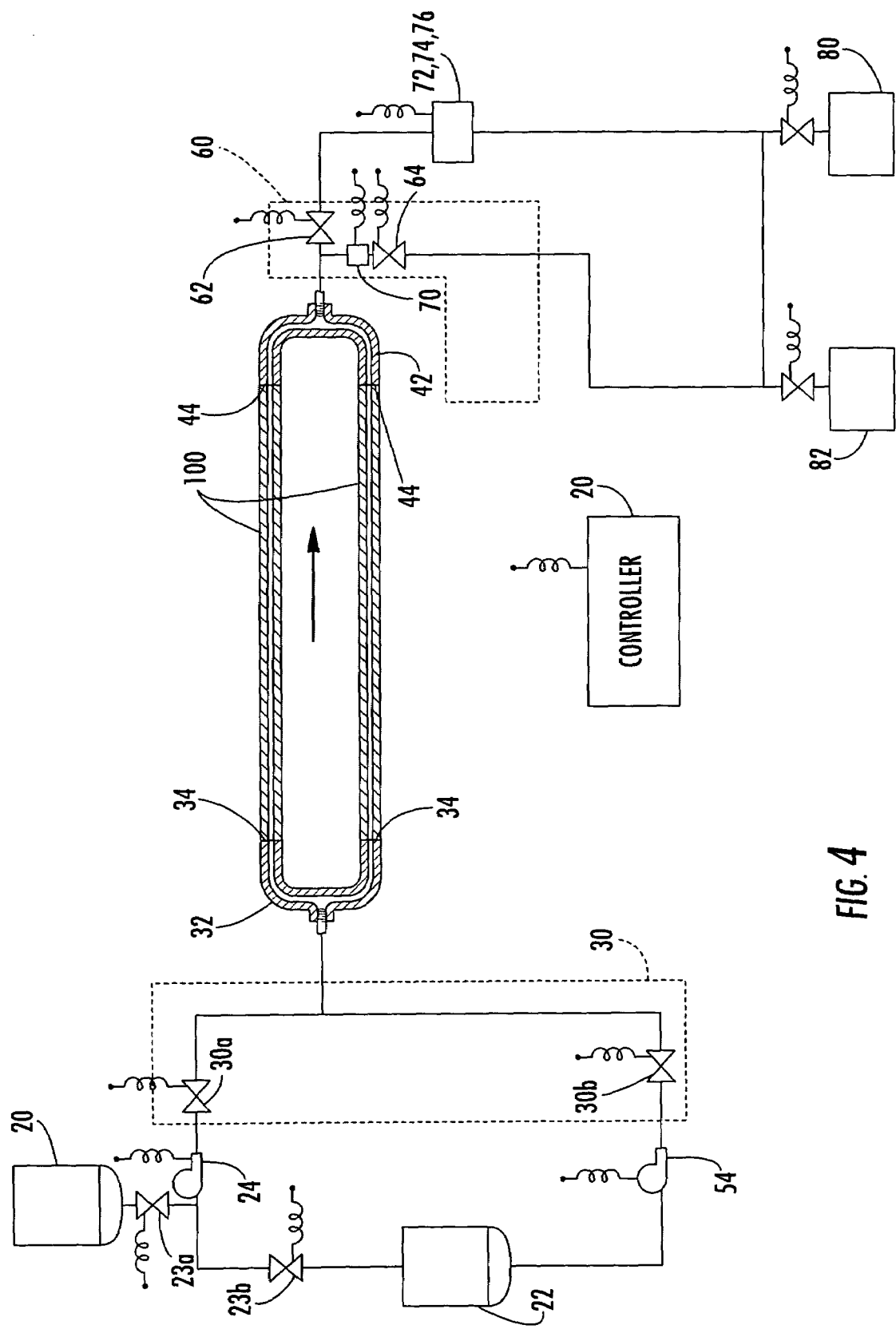

Having thus described the invention in general terms, reference will now be made to the accompanying drawings, which are not necessarily drawn to scale, and wherein:

FIG. 1 is a schematic diagram showing one embodiment of the invented apparatus;

FIG. 2 is a schematic diagram showing an alternative embodiment of a portion of the apparatus designed for use with a purge fluid and purge gas;

FIG. 3 is a schematic diagram showing another alternative embodiment of the apparatus capable of fluid recycle; and, FIG. 4 is a schematic diagram showing the embodiment of FIG. 1, but demonstrates the implementation of the apparatus with an automated controller.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring to FIG. 1, according to one embodiment, the apparatus generally comprises a cleaning fluid supply pump 24 and a pressurization pump 54 that are alternatively placed in communication with a feed header 32 by operation of valves 30a, 30b of a feed valve network 30. Supply lines to the cleaning pump 24 are valved such that the cleaning pump may receive a feed of cleaning solution from a cleaning solution reservoir 20 or a rinsing solution reservoir 22 where the rinsing solution is typically deionized (DI) water. The pressurization pump 54 receives a feed from the rinsing solution reservoir 22.

Fluid is supplied, under pressure, from either of the pumps 24,54 through the feed valve network 30 to the feed header 32. The feed header 32 has at least one but advanageously multiple feed header interfaces 34 engageable to the inlet end of at least one tubular structure 100 such that the inside of the at least one tubular structure is placed in fluid communication with the feed header 32.

A drain header 42 has at least one but advantageously multiple drain header interfaces 44 engageable to the outlet end of the at least one tubular structure 100 such that the inside of the at least one tube is temporarily placed in fluid communication with the drain header 42. The drain header 42 has an outlet in communication with an outlet valve network 60. The outlet valve network 60 comprises two main high-pressure valves. Flow through valve 62 provides communication from the drain header 42 to a fluid catch basin. The catch basin may be the same for each fluid used during cleaning of the tubes, or a separate catch basin may be used for each particular fluid used, for instance a cleaning solution basin 80 and a rinsing solution basin 82. Drain valve 64 provides a second pathway to a catch basin, for instance the rinsing solution catch basin 82, or simply to an external drain.

A pressure gauge 70 is advantageously in line with the fluid flow of the system and located between the outlet of the drain header 42, the flow through valve 62, and the drain valve 64. The gauge 70 is used to measure test pressure of the fluid during the pressure testing phase of the apparatus.

A number of analytical instruments are advantageously placed in line with fluid flow between the flow through valve 62 and the catch basins 80,82 for use during the cleaning phase of the operation. For instance, a particle counter 72 may be used to monitor the presence of particles within the effluent stream of cleaning solution or rinsing solution flowing out of the tube. A non-volatile residue (NVR) analyzer 74 may be used to monitor the presence of chemical coatings, degreasing agents, or other materials being washed from the inside of the tube. Also, a flow meter 76 is advantageously used to monitor the flow rate of cleaning solution or rinsing solution flowing through the tubular structure during the cleaning phase.

Still referring to the embodiment of FIG. 1, the apparatus has two primary operating phases, a cleaning phase and pressure testing phase. In the cleaning phase, the cleaning pump 24 is placed in fluid communication with the feed header 32 by opening valve 30a and closing valve 30b. The feed to the cleaning pump 24 is initially provided from the cleaning solution reservoir 20 by opening valve 23a and closing valve 23b. The cleaning solution is advantageously heated, such as to a temperature of between 140° F. and 180° F. Cleaning solution is pumped by pump 24 through the feed header 32 and into and through the at least one tubular structure 100. Cleaning solution continues to flow through the tubular structure 100, through the drain header 42, and through the outlet valve network 60 where valve 64 is set in the closed position and valve 62 is open to allow continuous fluid flow through a particle counter 72, NVR analyzer 74, and flow meter 76, if any. Finally, the cleaning fluid is allowed to flow out into the appropriate catch basin. The catch basin may include an oil separator or oil skimmer to allow longer use between solution changes.

As the second step in the cleaning phase, the feed fluid to the cleaning pump 24 is changed to a rinse fluid, such as DI water, by closing valve 23a and opening valve 23b to the rinsing fluid reservoir 22. The cleaning phase continues as above except that the rinsing fluid may be diverted to a separate rinsing fluid catch basin after passing through the apparatus.

After the inside of the tube 100 has been determined to be acceptably clean, as described below, both the flow through valve 62 and the drain valve 64 are closed while rinsing fluid remains in the tube 100. To begin the pressure testing phase of the operation, valve 30a is closed and valve 30b is opened to place the pressurization pump 54 in communication with the feed header 32. The pressurization pump 54 is activated and draws a feed from the rinsing fluid reservoir 22. Since the apparatus is no longer set up in a flow through configuration, the pressurization pump 54 will only draw a small amount of rinsing fluid from the reservoir while pressurizing the fluid within the tube. Pressurization of fluid within the tube 100 is measured by the pressure gauge 70, and may also be roughly determined by knowing the pump speed of the pressurization pump 54. Use of rinsing fluid as the pressurization fluid provides an overall reduction in fluid that must be recycled or disposed of because the apparatus and tubes need not be filled with a separate pressurization fluid for pressure testing as required in traditional hydrostatic-type testing methods.

The one or more tubular structure 100 are pressurized to an extent in accordance with manufacturers' specifications or other specifications designed to ensure the suitability of the tubular structure for their intended purpose. Typically, parts designed for use in critical applications will be tested at pressures of 1.5× the design operating pressure. Typically, pressure will be placed and held on the parts for five repetitions of one to five minutes for each pressurization cycle. The system may incorporate a timer that can control drain valve 64 to relieve pressure and to pressurize the test item to the required pressure. A relief valve or other safety pressure relieving devise should be installed downstream of feed header 32 to protect the system in the event of accidental over pressurization.

After pressure testing is complete, the fluid may be drained from the tubes and portions of the apparatus by opening drain valve 64. The pressure tested fluid may be collected in a catch basin or sent to an external drain.

The cleaning pump 24 of the apparatus is any pump capable of propelling a volume of fluid through the attached tubes 100 that might act to dislodge particulates within the tube and to wash away any unwanted coatings or residues within the tube. Typically, a pump is used with the capacity to provide flowrates of 400 US gallons/minute at 50 PSI. An exemplary pump motor would provide 20 HP as 3600 RPM. A 10 micron filter may be attached to the outlet of the pump to filter out any particulates in either the cleaning fluid or the rinsing fluid. Further, exemplary pumps might be selected from air driven pumps such as those made by Haskell International or a commercially available electric motor driven pump such as the Motor Speed Series Internal Gear Pumps offered by Viking Pump, Inc., Cedar Falls, Iowa.

The pressurization pump 54 of the apparatus is any pump or device capable of increasing the pressure of the fluid filled tube, and interceding portions of the apparatus, to the desired test pressure of the tube being tested. An accumulator capable of providing the required pressure may be used in lieu of a pressurization pump. Typical required pressures range from 500-20,000 PSIG. An exemplary pump is Haskell International (Burbank, Calif.) Air Driven Liquid Pump Model 8HP, capable of providing pressures up to 22,000 PSI.

Each of the main pressure control valves of the apparatus, particularly valves 30a, 30b, 62, and 64, are subject to pressure during the pressure testing phase of the operation. The valves are preferably solenoid operated high-pressure valves that are normally opened so that system pressure will be relieved in the event of power loss. Such valves are commercially available from numerous providers.

The interfaces of the feed and drain headers are capable of temporarily connecting the respective ends of tested tube structures to the headers 32, 42 in such a manner that significant leaking of fluid from the interface does not occur during the cleaning of the pressure testing phase. An exemplary high-pressure interface is Autoclave Engineers, Inc., part number F-250-C.

The cleaning solution used in the apparatus may be any solution capable of dislodging particulates within the tubes being cleaned or of dissolving and carrying away contaminants such as greases, coatings, lubricants, etc. For instance, for tubes having water soluble contaminants, a heated pure water or other aqueous cleaning solution may be used. For tubes having oil soluble contaminents, a solution capable of removing oil based compounds may be used. An exemplary cleaning solution for use with oil soluble contaminants is Turco™ 4215, available from Henkel Surface Technologies Corporation, Madison Heights, Mich.

The rinsing solution is advantageously water or an aqueous solution. As shown in FIG. 1, the pressurization pump 54 advantageously draws fluid from the rinsing solution reservoir 22, though, as shown in FIG. 2, the pressurization pump 54 may instead draw any needed additional fluid from a separate reservoir 56 and the fluid used by the pressurization pump 54 may or may not be the same fluid as the rinsing fluid. The cleaning and rinsing solutions are preferably supplied by the same pump, but the solutions may be provided with separate pumps corresponding to each solution.

Still referring to FIG. 2, an alternative embodiment of the apparatus is shown in which the use of an additional purge fluid and purge gas are demonstrated. A purge solution and purge gas may be used individually, collectively, or not at all in operation of the apparatus. The use of both purge fluid and purge gas are described herein together for ease of description.

Operation of the alternative embodiment is substantially the same as that of the embodiment of FIG. 1, with the following exceptions. After the pressurization phase of the operation, valve 30b is again closed. Purge fluid is flowed through the apparatus and tube by opening valves 23c and 30a (all other valves shown in FIG. 2 are closed) and pumping the purge fluid from the purge fluid reservoir 26 through cleaning pump 24 and into the feed header as with cleaning solutions specified above. After purging with the purge fluid, a purge gas is optionally passed through portions of the apparatus and the tube in order to quickly remove any liquid remaining within the tube. The purge gas may be heated to aid in the removal of clean or rinsing solutions. To purge with purge gas, the cleaning pump is isolated by closing valve 30a and valve 30c is opened thereby allowing a pressurized purge gas stream to flow through the feed header and tube from a purge gas supply 28. After flowing through the apparatus, the purge gas may be recaptured or vented to the environment. After the gas purge, valve 30c is closed and the tube may be removed from the apparatus.

The purge fluid may be a liquid having volatility greater than the rinsing solution such as a VOC solvent. The flow of purge fluid displaces residual rinsing fluid from within the tube. The residual fluid remaining within the tube after the fluid purge either evaporates under environmental conditions, or is easily volatilized by a subsequent gas purge. The purge gas may be any gas that is non-reactive with the other solutions used in this process and which does not readily condense inside the tube under process conditions. Dry gaseous nitrogen is a preferred purge gas. The nitrogen may be heated to aid in the removal of liquids. Nitrogen is advantageous because it is readily available and inexpensive. Helium or compressed air may also be advantageously used.

Referring to FIG. 3, according to another alternative embodiment of the apparatus, any of the spent cleaning, rinsing, pressurizing, or purge fluids may be recycled by the apparatus rather than being simply collected in catch basins or otherwise disposed of. The fluids may be recycled by a fluid recycle stream 96,98 back to the cleaning fluid supply pump 24 or fluid reservoirs 20,22. The fluids may be filtered, cleaned, or otherwise purified by a treatment device 90,92 in line with the fluid recycle stream before being reused by the apparatus. It is particularly advantageous to filter the recycled cleaning fluid stream using a filter 90 since this stream is the most likely to contain suspended particulates removed from the inside of previously cleaned parts. Where two or more fluids have mixed during operation of the apparatus, the components of the fluids may be separated as part of the recycling process before reuse.

The degree to which the inside of the tubes must be cleaned will vary with the intended use of the tube. In some situations, it will be known from experimentation or prior knowledge what flow rates and amounts of cleaning and rinsing fluids are required in order to adequately clean the tube. In such circumstances, the apparatus may advantageously provide predetermined, timed flowrates of fluids through the apparatus, either manually controlled or automatically controlled, after which the tube would be deemed to be acceptably clean and fit for service. Alternatively, sensors such as the particle counter 72 or NVR analyzer 74 may be used to determine purity of an effluent stream in order to determine the cleanliness of the interior of the tube being processed. An NVR analyzer tests for carbon based materials that would be incompatible with oxygen and oxidizer systems. An exemplary requirement might be that no particle larger than 100 microns in size be contained in the effluent liquid after cleaning. Cleanliness requirements vary according to the type pf hardware being cleaned and the intended service.

Referring to FIG. 4, the operation of the apparatus in general is advantageously automated by use of a controller in operative communication with the major components of the apparatus. In particular, the controller is capable of receiving inputs from the pressure gauge 70, particle counter 72, NVR analyzer 74 and flow meter 76 to determine the status of the cleaning and/or pressurization processes. The controller may engage/disengage the valves 23a, 23b, 24, 30a, 30b, 62, and 64, and engage, disengage, or vary the speed of pumps 24,54 to alter the operation of the apparatus in the manner generally described above.

The apparatus and method are particularly useful for simultaneously cleaning and pressure testing multiple production parts. By providing the feed and drain headers with multiple interfaces, a large number of production parts may be connected between the headers and simultaneously cleaned/tested in accordance with the invention. The ability to clean and pressure test a large number of production parts without having to reconfigure or reattach the production parts within a cleaning or testing apparatus provides significant time savings relative to traditional cleaning and testing methods.

The invented apparatus may be installed in a fixed location or the apparatus may be situated on a mobile frame so as to be movable throughout a test area or manufacturing facility. If assembled on a mobile cart, the reservoirs of fluid described above may be located on the cart or, alternatively, the fluid supplies may be external to, but connectable with, the cart.

Many modifications and other embodiments of the invention will come to mind to one skilled in the art to which this invention pertains having the benefit of the teachings presented in the foregoing descriptions and the associated drawings.

Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for cleaning and pressure testing tubular structures with a common apparatus, the steps comprising:
providing a cleaning and pressure testing apparatus having a cleaning fluid reservoir, and a rinse fluid reservoir, and wherein the cleaning fluid and rinse fluid reservoirs are configured to be in fluid communication with one or more catch basins;
engaging a first end of at least one tubular structure to an output interface of the apparatus;
engaging a second end of the at least one tubular structure to an input interface of the apparatus;
maintaining engagement of the first and second ends of the at least one tubular structure with the apparatus while sequentially
flowing a cleaning fluid from the cleaning fluid reservoir through an interior of the tubular structure and into the catch basin;
flowing a rinse fluid from the rinse fluid reservoir through the interior of the tubular structure;
preventing the rinse fluid from flowing into the one or more catch basins;
pressurizing the rinse fluid within the tubular structure; and
monitoring the pressure of the rinse fluid while the rinse fluid is pressurized within the tubular structure.

2. The method of claim 1, further comprising the step of providing the cleaning fluid, under pressure, from a cleaning fluid supply pump, thereby causing the fluid to flow through the tubular structure.

3. The method of claim 2, further comprising the step of supplying cleaning fluid to the cleaning fluid supply pump from the cleaning fluid reservoir.

4. The method of claim 1, further comprising the step of analyzing the cleaning fluid after the cleaning fluid has flowed through the tubular structure.

5. The method of claim 4, wherein the step of analyzing comprises use of an instrument selected from a particle counter, a non-volatile residue (NVR) analyzer, and combination thereof.

6. The method of claim 1, further comprising the step of monitoring the flow rate of the cleaning fluid as the cleaning fluid flows through the tubular structure.

7. The method of claim 1, further comprising the step of flowing the rinse fluid through the tubular structure subsequent the step of flowing cleaning fluid through the tubular structure but prior to the step of pressurizing the rinse fluid within the tubular structure.

8. The method of claim 7, further comprising the step of providing the rinse fluid, under pressure, from a cleaning fluid supply pump, thereby causing the rinse fluid to flow through the tubular structure.

9. The method of claim 8, further comprising the step of supplying rinse fluid to the cleaning fluid supply pump from a rinse fluid reservoir.

10. The method of claim 1, wherein pressurization of the rinse fluid is provided by a pressurization pump.

11. The method of claim 1, further comprising the step of draining cleaning fluid from the at least one tubular structure subsequent to pressurizing the rinse fluid.

12. The method of claim 1, wherein engaging the first and second ends of the tubular structure comprises engaging the first and second ends of the tubular structure with the interfaces of the apparatus such that the apparatus is in fluid communication with the interior of the tubular structure and the interior of the tubular structure is isolated from the external environment.

13. The method of claim 1, further comprising the step of flowing purge fluid through the tubular structure subsequent the step of flowing cleaning fluid through the tubular structure.

14. The method of claim 13, wherein the step of flowing purge fluid through the tubular structure occurs prior to the pressurization step.

15. The method of claim 13, wherein the step of flowing purge fluid through the tubular structure occurs subsequent the pressurization step.

16. The method of claim 13, further comprising the step of flowing a purge gas through the tubular structure subsequent to the step of flowing a purge fluid through the tubular structure.

17. The method of claim 1, further comprising the step of recycling spent cleaning fluid within the apparatus.

18. The method of claim 1, further comprising the step of controlling the fluid flow and pressurization within the apparatus with an automated controller.

19. The method of claim 1, wherein the rinse fluid is pressurized to a pressure that is about 1.5 times of a design operating parameter of the tubular structure.

* * * * *